US007261103B2

(12) United States Patent
Katz

(10) Patent No.: US 7,261,103 B2
(45) Date of Patent: Aug. 28, 2007

(54) COMBINED TONGUE DEPRESSOR AND ORAL SPRAY DEVICE

(76) Inventor: Harold Katz, 370 S. Fairfax Ave., Los Angeles, CA (US) 90036

( * ) Notice: Subject to any disclaimer, the term of this patent is extended or adjusted under 35 U.S.C. 154(b) by 858 days.

(21) Appl. No.: 10/650,314

(22) Filed: Aug. 28, 2003

(65) Prior Publication Data

US 2004/0044303 A1 Mar. 4, 2004

Related U.S. Application Data

(60) Provisional application No. 60/406,466, filed on Aug. 28, 2002.

(51) Int. Cl.
*A61M 15/00* (2006.01)

(52) U.S. Cl. ............................ 128/200.15; 128/200.23

(58) Field of Classification Search ........... 128/200.15, 128/200.14, 200.21, 200.23; 239/338, 390–394; 604/77; 222/533, 536
See application file for complete search history.

(56) References Cited

U.S. PATENT DOCUMENTS 3,148,806 A * 9/1964 Meshberg .............. 222/402.11
5,746,197 A * 5/1998 Williams ............... 128/200.23
6,067,936 A * 5/2000 Margulis .................... 119/201
6,105,826 A * 8/2000 Oursin et al. .......... 222/153.06
6,158,431 A * 12/2000 Poole .................... 128/203.12
7,025,232 B2 * 4/2006 Green ..................... 222/321.7

* cited by examiner

*Primary Examiner*—Steven O. Douglas
(74) *Attorney, Agent, or Firm*—J. Harold Nissen; Lackenbach Siegel, LLP

(57) ABSTRACT

A combined tongue depressor and oral spray adapted to be connectable to a container containing an oral spray material to enable material contents contained within the container to be dispensed through the tongue depressor and oral spray to reach a throat cavity and a rear portion of the tongue, including a universally moveable longitudinal tube member having an inner passageway extending from a proximal and thereof to a distal end thereof; the proximal end being connected to the container for permitting universal movement of the longitudinal tube relative to the container; and a material exit associated with the distal end of the longitudinal tube for permitting material contained in the container to exit from the container and pass through the tube and out of the tube to reach the rear of the tongue and the throat cavity and the rear of the mouth.

20 Claims, 8 Drawing Sheets

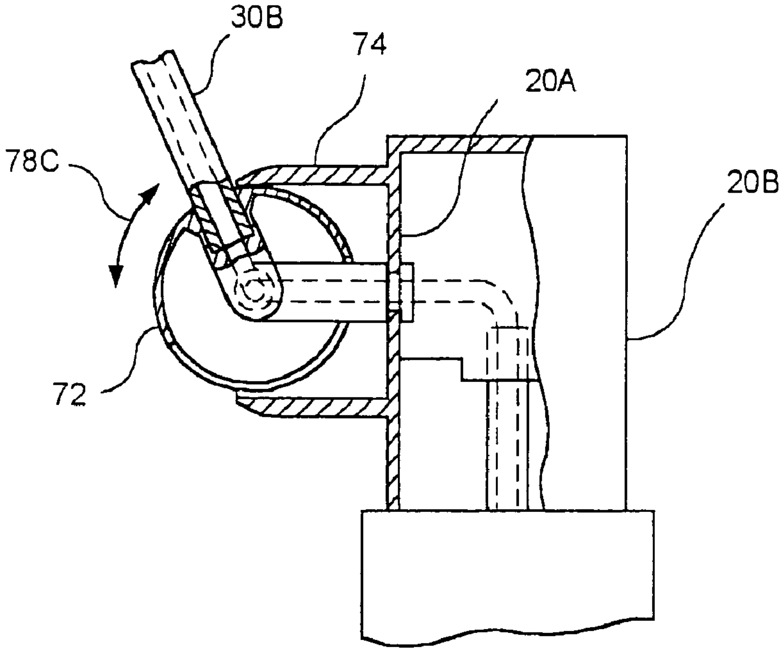
F I G. 19
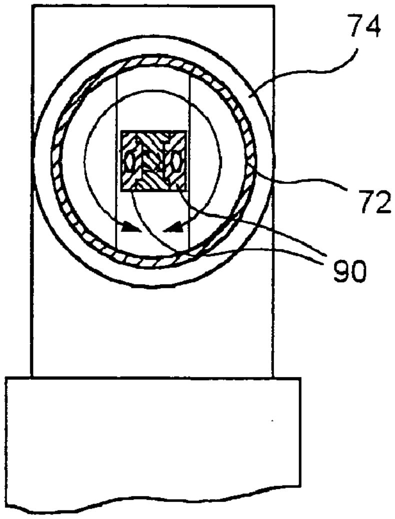
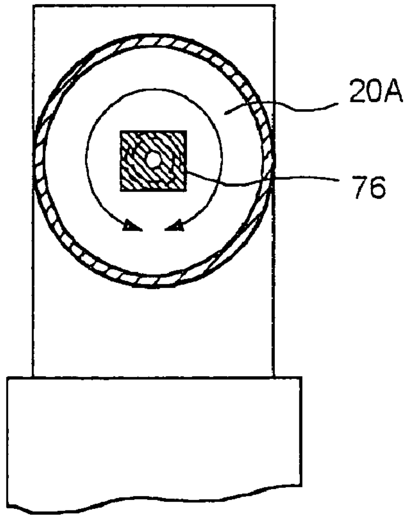
F I G. 20
F I G. 21

COMBINED TONGUE DEPRESSOR AND ORAL SPRAY DEVICE

CROSS-REFERENCE TO RELATED APPLICATION

This invention claims priority from Provisional Patent Application No. 60/406,466, filed in the name of the inventor Dr. Harold Katz on Aug. 28, 2002.

BACKGROUND OF THE INVENTION

1. Field of the Invention

This invention is concerned with a combined tongue depressor and oral spray mechanism which is used to dispense or spray a solution or fluid, such as a liquid, a gel, a gel paste or any other material so that the rear portion of the throat area, and the rear portion of the tongue, tonsil area or pharynx can be reached by the material being sprayed.

2. Description of Prior Art

Conventional oral spray devices use a spray head which just about enters the forward or opening mouth portion, and the spray or material dispensed does not reach the throat portion, tonsil area or the dorsal or rear portion of the tongue or the pharynx area. Specifically, the spray may also be blocked by the tongue raising its position in the mouth cavity. Moreover, when a conventional spray head is used, the spray portion or item dispensed spreads and contacts the posterior portion of the tongue and does not reach the rear of the mouth and the effectiveness of the oral spray, i.e. item dispensed is dissipated. It has also been found that when a conventional spray head or dispenser is used the user's tongue also tends to prevent the spray or dispensed item from reaching the pharynx, tonsil area, throat or rear portion of the mouth where the tonsils are located, and as well as the dorsal portion of the tongue.

To use a conventional tongue depressor, together with a dispensing mechanism or spray device, both individually would be cumbersome for a user.

It has also been found that heretofore conventional spray devices may be difficult to manipulate because the orientation of the spray nozzle may be difficult to adjust based on the connection between the spray nozzle and the material container.

BRIEF SUMMARY OF THE INVENTION

In order to avoid the deleterious effects of conventional spray devices, I have developed a combined tongue depressor and oral spray device or dispensing device which can be used by individuals having the requirement for different angular usages. In one of the preferred embodiments, the device can be used by individuals having a different sized mouth cavity.

The purpose of the combined tongue depressor and oral spray is to provide for a head portion or discharge nozzle at the distal end of the mechanism so as to have or enable the oral spray which includes any product or material that is dispersed or can be dispersed through a nozzle opening to reach the intended area without having the tongue prevent the spray or dispensed product from reaching the throat portion, while the proximal end of the mechanism is close to a container containing the fluid or item to be dispensed.

The oral spray which is intended to be dispersed by the inventive combined tongue depressor and oral spray dispenser because the material to be dispensed is intended primarily to reach a particular area of a person's mouth and oral cavity. To be most effective, it is intended that the material reach the rear of the mouth cavity as explained. The oral spray to be dispensed or item to be dispensed is to be distinguished from other oral sprays and dispensed items wherein location or intended areas may not be as sensitive as the intended area for the dispersion of the oral spray to be dispersed with the combined tongue depressor and oral spray dispenser.

For the utility of the material dispensed, the rear of the mouth cavity is the most important area to be reached and the tongue has a tendency to block the opening to the rear portion of the mouth cavity.

The combined tongue depressor and oral spray mechanism includes a distal end portion which provides a mechanism having one or more orifices to dispense the fluid and is connected with a central portion having an inner passageway through which the material or fluid can pass from its entry portion at the proximal end of the central portion to the exit portion at the distal end. A movable connection is provided for connecting the proximal end of the central portion to a fluid container having a fluid dispensing mechanism.

In accordance with the teachings of this invention, the combined tongue depressor and oral spray mechanism can be adjusted for any individual mouth cavity and for any different angular control.

The combined tongue depressor and oral spray mechanism may have a cylindraceous or a quadrangular outer configuration with a round portion outer configuration, an oval outer configuration or at least one flat portion outer configuration adapted to engage or rest on top of the tongue portion or any other outer configuration suitable to be applied to the upper surface of the tongue portion, if necessary to prevent any part or portion of the tongue from interfering with the spray discharged from the discharge nozzle at the distal end.

The central portion in one embodiment for universal usage is preferably about three inches in length to enable the distal end portion with the nozzle to reach the throat cavity and the dorsal portion of the tongue. This is for an adult. For a child, the length extent may be approximately one inch. For this purpose, the present invention proposes another embodiment having an adjustable central portion. In one preferred embodiment, a telescopic arrangement is used to provide for the length adjustment. This avoids the necessity of having different sized devices for different individuals.

It is important to appreciate that the tongue may prevent the dispensed product from reaching the rear of the mouth as set forth above. It is important for the product or material to reach down deep into the throat portion of the individual.

The present invention overcomes the problem of "Gag Reflex" which happens substantially automatically when any foreign object touches a sensitive area in the back of ones throat and the rear portion of the tongue.

To understand the purpose of the present invention in more detail, it is necessary to consider the problems in connection with bad breath.

Bad breath is caused by Anaerobic Sulfur Producing Bacteria which normally live WITHIN the surface of the tongue and in the throat. These bacteria are supposed to be there, because they assist humans in digestion by breaking down proteins found in specific foods, mucous or phlegm, blood, and in diseased or "broken-down" oral tissue. Under certain conditions, these bacteria start to break down proteins at a very high rate. Proteins are made up of Amino Acids. Two of the Amino Acids, Cysteine and Methionine, are dense with sulfur. It is these Amino Acids which are not desired and can cause problems.

When these "beneficial" bacteria come into contact with these compounds, the odorous and "bad-tasting" sulfur compounds are released from the back or dorsal portion of the tongue and throat, as Hydrogen Sulfide, Methyl Mercaptan, and other odorous and bad tasting compounds. These "problem" compounds are often referred to as Volatile Sulfur Compounds (VSC), where volatile means Vaporous and Effervescent, two adjectives which accurately describe their ability to offend other people instantly.

An understanding of Bacteriology will explain a very important fact about these "bugs." These are not "bad guys"—they are not infectious. Everyone in the world has the same group of bacteria in their mouth. You cannot "catch" bad breath from someone else—even by kissing. Since they are part of our normal oral flora, you cannot permanently remove them from your mouth—not by tongue scraping, not by antibiotics, and not by rinses which claim to "lift the bacteria off your tongue". The only scientifically proven and clinically effective method of halting Halitosis is by attacking the bacteria's ability to produce VSC and by converting the VSC into non-odorous and non-tasting organic salts.

I have found that with present sprays and tongue scrapers the dorsal portion of the tongue and the throat cavity still harbor these bad "bugs", and I have tried to solve the problem to eliminate the development of the VSC.

The anaerobic bacteria not only live on the tongue and in particular at the dorsal portion of the tongue, but are located in the rear portion of the mouth cavity. Use of a conventional spray head does not reach the rear of the mouth cavity, and therefore the entire effectiveness of the oral spray only reaches part of the intended area within the mouth cavity. Moreover, with a conventional spray head, the tongue tends to block the spray and prevent it from reaching the rear of the mouth cavity.

It is therefore the purpose of this invention to provide an oral spray mechanism which can reach the throat cavity for dispensing a material such as a fluid, a liquid in a mass or a gel of droplets or a gel paste or any material which may be discharged, as discharged from a pressurized container having an exit orifice.

Yet a further important purpose of my invention is to stop bad breath due to activity at the tonsil area, throat portion and rear portion of the tongue so as to neutralize the sulphur compounds that were created by the anaerobic bacteria that live in the deep recesses of the throat, tongue and tonsil area.

It is a further purpose of this invention to provide a combined tongue depressor and oral spray to permit the contents of a pressurized or non-pressurized container to have the fluid or gel contents thereof to be discharged as the oral spray in order to reach the rear of the mouth cavity without having the tongue interfere with the oral spray.

BRIEF DESCRIPTION OF THE DRAWINGS

In order that the invention may be more fully understood, and to have its purposes and advantages become readily apparent, reference is made to the following detailed description of the preferred embodiments illustrated in the accompanying drawings.

FIG. 19 is a partial sectional view similar to FIG. 17 but showing the tongue depressor portion moved from the position shown in FIG. 17;

FIG. 20 is a partial sectional view taken along 20-20 of FIG. 17; and FIG. 21 is another partial sectional view taken along line 21-21 of FIG. 17.

DETAILED DESCRIPTION OF THE PREFERRED EMBODIMENT

Figure 2:
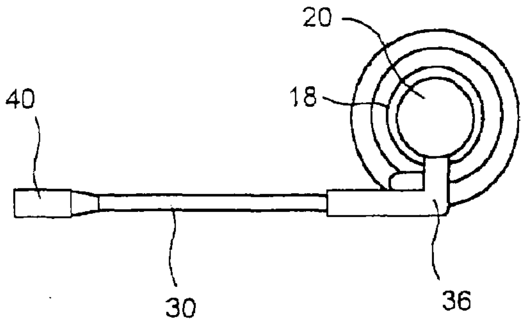
FIG. 2 is a top view of the combined tongue depressor and oral spray mechanism of FIG. 1, and showing the fluid or liquid content container, closure cap and the tongue depressor and oral spray mechanism in the one full outline situation looking down to the container shown in FIG. 1.
Figure 1:
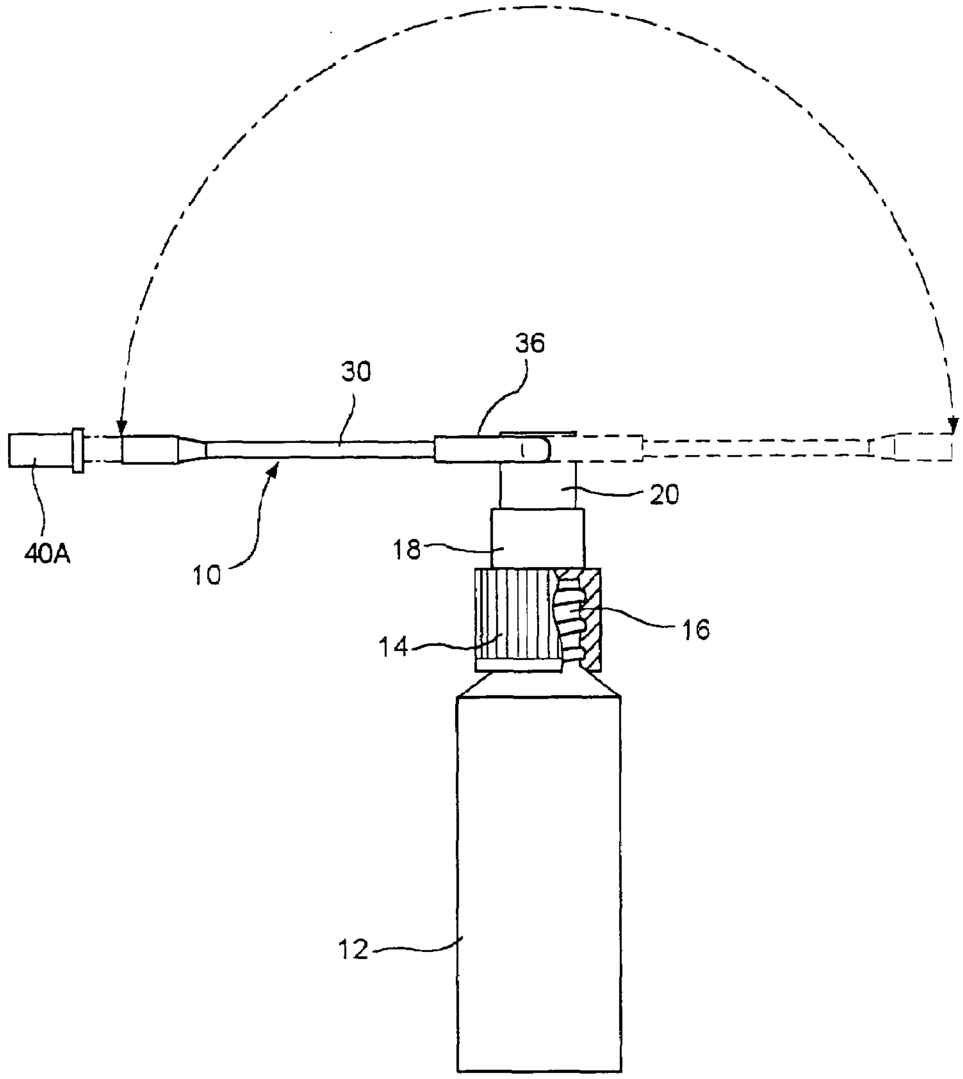
FIG. 1 is a front elevational view of one embodiment the combined tongue depressor and oral spray mechanism shown attached to a container adapted to contain a spray liquid with the mechanism shown in full outline in one position and in dashed outline displaced 180° from the full outline position.

Referring now more particularly to the accompanying drawings and in particular to FIG. 1 which shows one embodiment of one of the best modes presently contemplated for carrying out the invention, the combined tongue depressor and spray device 10 is shown attached to or associated with a fluid container 12 for containing the liquid or fluid to be dispensed and sprayed through device 10.

As best seen in FIG. 1, the combined tongue depressor and oral spray device, device 10, is connected with container 12 which is adapted to contain the liquid or fluid to be sprayed. Closure member 14 closes inner extension portion 16 of container 12 which is an entry portion extension from container 12 and entry-exit portion for the material contained within the container. Closure member extension portion 18 forms part of the fluid dispensing mechanism and is coupled with closure device 14 and is a guideway for pressure member 20 connected with longitudinal tube 30.

Figure 3:
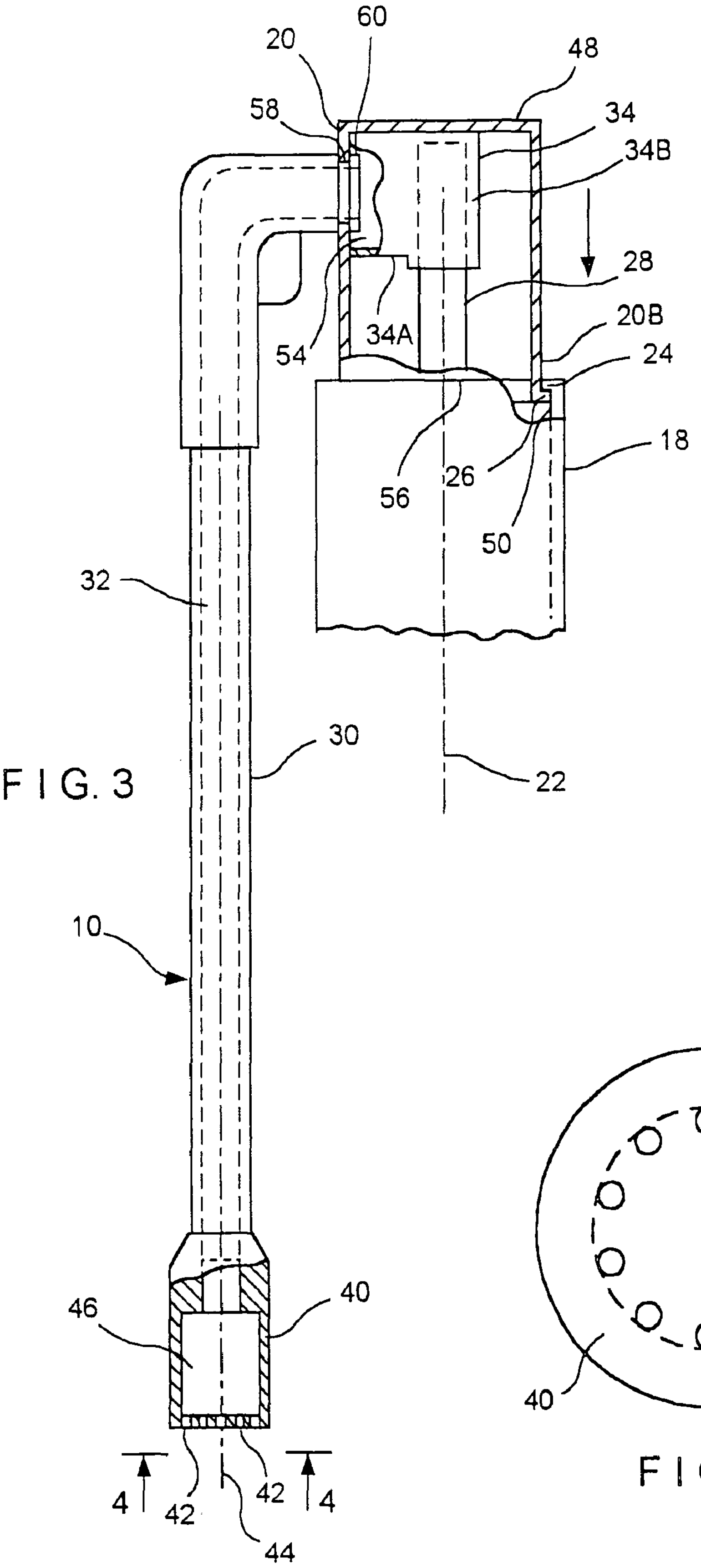
FIG. 3 is a front view partially in section of the fluid or liquid exit discharge nozzle as shown in FIG. 1 and the connection to the container containing the fluid or liquid contained in the container to be dispensed by the combined tongue depressor and oral spray mechanism illustrating the exit orifice.

Referring now more particularly to FIG. 3 which shows extension portion 18 and pressure member 20, extension portion 18 provides a guideway for pressure member to move both in a vertical direction relative to a central axis 22 which coincides with a central axis of container 12, and also permits and confines rotation of pressure member about the central axis 22. Pressure member 20 is rotatable relative to extension portion 18 and is movable axially along axis 22 relative to extension portion 18.

Extension portion 18 has an outer extending portion 24 which is in contact with the outside surface of pressure member 20 and pressure member 20 has an outwardly extension portion 26 which cooperate with each other for guiding and preventing the pressure member from becoming disconnected from extension portion 18.

The outwardly extension portion 26 which cooperates with outer extending portion 24 prevents pressure member 20 from becoming dislodged from closure member extension portion 18.

Outwardly extension portion 26 and outwardly extending portion 24 cooperate to guide the movement of pressure member 20 relative to closure member extension portion 18 both rotationally about axis 22 and longitudinally along axis 22.

Closure member 20 includes a central tubular member 28 which communicates with longitudinal tube 30 and container 12 so that pressure created by pumping action of pressure member 20 causes the contents of container to enter into central opening 32 of longitudinal tube 30.

Extension portion 18 is connected with member 14 to permit movement of pressure member 20 relative to extension portion 18. Pressure member 20 is rotatable relative to extension portion 18 and is movable axially related to the longitudinal axis of container 12 during both the pumping action and non-pumping action of pressure member 20. Extension portion 18 of the dispensing mechanism is connected with closure 14 and permits rotation of pressure member 20 through an arc of 360° about the longitudinal axis of container 12. Pressure member 20 is coupled with extension portion 18 and is used to cause the contents in the in container to be expelled by vertically pushing pressure member 20 relative to closure member 14 and extension portion 18.

Tongue depressor and oral spray device 10 is swively connected to pressure member 20 and is rotatable through an arc of 360° about an axis perpendicular to longitudinal axis 22 of pressure member 20. The spray device 10 may also be considered to be swively connected with pressure member 20.

The combined movements of the tongue depressor and oral spray device 10 and pressure member 20 relative to container 12 which is hand-held permits sufficient movement of device 10 relative to container 12 so that the rear portion of the mouth can be sprayed with ease.

As best seen in FIG. 3 which schematically shows the plunger mechanism which includes pressure member 20 and is shown partially in section and includes an inner rim member defined by outwardly extending portion 26. Pressure member 20 cooperates with closure member extension portion 18 which is provided with outer extending portion 24 facing towards the central axis 22. Portion 26 is pressure fitted within the inner portion of outwardly extension portion 26 and is held by frictional engagement with inner rim member 50 of closure member extension portion 18, and outwardly extending portion 24 is in engagement with outer surface 52 of pressure member 20.

Pressure member 20 includes a roof portion 48 having internally thereof an L-shaped fluid guide member 34 extending therefrom which directs the material from central tubular member 28 to longitudinal tube 30. Fluid guide member 34 surrounds central tubular member 28 and has an opening or orifice 54 forming an outer tubular exit member from fluid guide member 34. Exit member or exit portion 56 of closure member 18 opens into central tubular member 28. Movement of pressure member vertically and axially about the central axis 22 of container 12 causes material to be expelled from the container 12.

Pressure member 20 as schematically shown is provided with an exit opening or orifice member 58 for communication with opening 54 of tubular member 28. Fluid guide member 34 is an L-shaped which has one leg 34*a* provided with an opening 62 surrounding orifice member 58 so that the material from container 12 and passing through central tubular member 28 can be expelled through the orifice 58 into longitudinal tube 30. Tubular member 28 is surrounded by the other leg 34*b* of L-shaped fluid guide member 34

L-shaped fluid guide shaped member 34 has its opening 58 opening into central opening 32 of longitudinal tube 30. Central opening 32 has one end opening into and communicating with exit orifice member 58.

Tongue depressor and oral spray device 10 generally includes an L-shaped rotatable coupling member 36 at one end of tube 30 which is swively connected with pressure member 20 so as to permit longitudinal tube 30 to be universally movable relative to pressure member 20 and container 12, and for this purpose longitudinal tube 30 is shown in one position in solid outline and in a position displaced 180° in dashed outline, but it should be noted that it can assume any number of conventional positions for its intended use as best seen in FIGS. 44 to 21.

Figure 8:
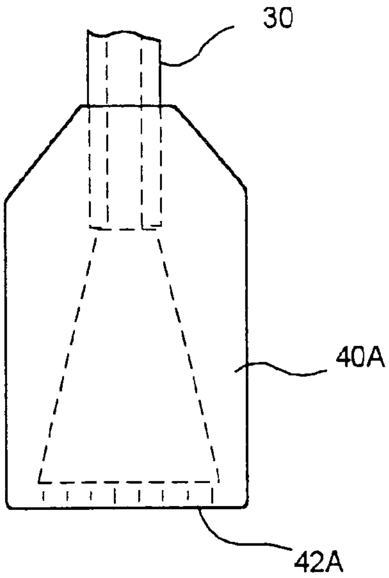
FIG. 8 is a partial elevational view of a modification of the dispensing spray nozzle 40 as shown in FIG. 1 and provided with an oval exit portion configuration and a plurality of exit orifices.
Figure 9:
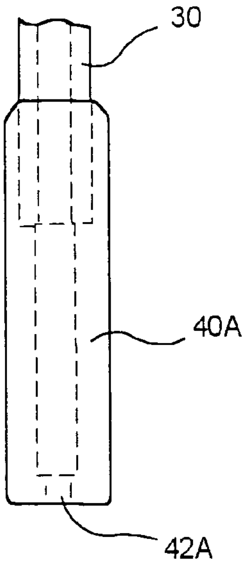
FIG. 9 is a side view of the modification shown in FIG. 8.
Figure 10:
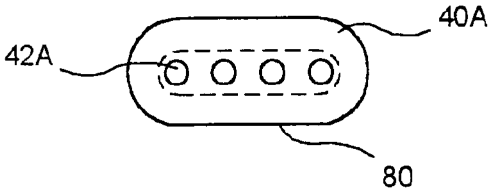
FIG. 10 is a bottom view of the exit portion of the outer oval shaped member attached to the longitudinal tube shown in FIG. 8.
Figure 13:
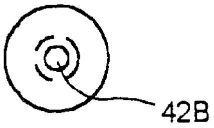
FIG. 13 is a bottom view of the embodiment of FIG. 11.
Figure 11:
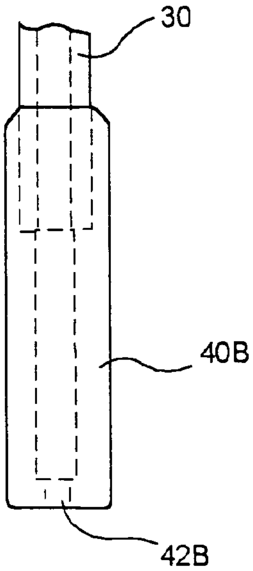
FIG. 11 is a partial elevational side view of a modification of the longitudinal tube of FIG. 8.
Figure 12:
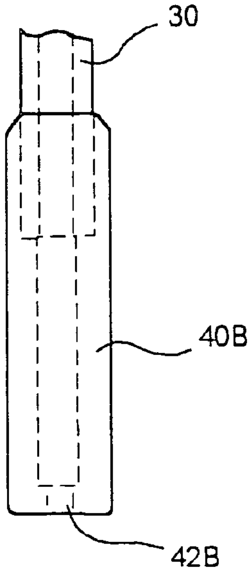
FIG. 12 is a side view of the longitudinal tube of FIG. 11.

Longitudinal tube 30 can have various cross-sectional configurations, and as noted in the first embodiment, as illustrated in FIGS. 1 to 5, has a circular outer configuration when a transverse section is taken perpendicularly to the longitudinal axis thereof, and as shown in FIGS. 11 to 13. In a similar manner, the outer configuration can have a square or rectangular or oval configuration when a transverse section is taken orthogonally to the longitudinal or central axis 44 of tube 30, an example of which is shown in FIGS. 8 to 10.

L-shaped member 36 as shown partially in section includes an extension portion 62 which is on the inside of pressure member 20 and adjacent to the outer rim portion of exit opening 58, so that it is rotatably connected with pressure member 20 of orifice member 56, and as seen in more detail in FIGS. 17 to 21, which shows a modification to provide L-shaped member 36 at one end thereof includes an undercut portion 64 which forms a rotable and connection with the edge of orifice member of pressure member 20 for a universal movement of longitudinal tube 30B so that tube 30 can be rotated through an angle of 360° relative to container 14. The inner portion of extension 62 includes an opening which communicates with opening 32.

Figure 4:
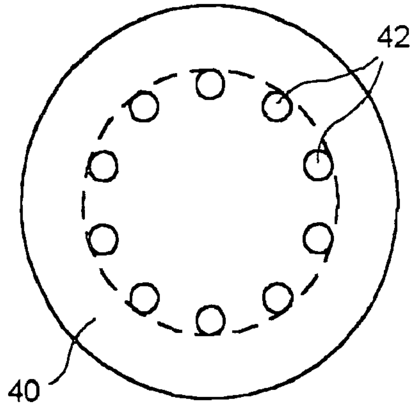
FIG. 4 is a partial schematic view facing the front of the nozzle shown looking in the direction of line 4-4 of FIG. 3 of the fluid or liquid exit from the nozzle portion of the combined tongue depressor and oral discharge.

Coupled to the other end of tube 30 is a dispenser spray nozzle 40 as best seen in FIGS. 3 and 4. Dispenser nozzle 40 is provided with openings 42 peripherally arranged about the central axis 44 coaxial with central opening 32.

Spray nozzle 40 may also be provided with a central opening 46 aligned with opening 32 for the discharge of the material from container 12.

As best shown in FIG. 1, the nozzle 40 may be provided with a cover 40A which is shown proximate to nozzle 40 and provides a cover therefore.

Figure 5:
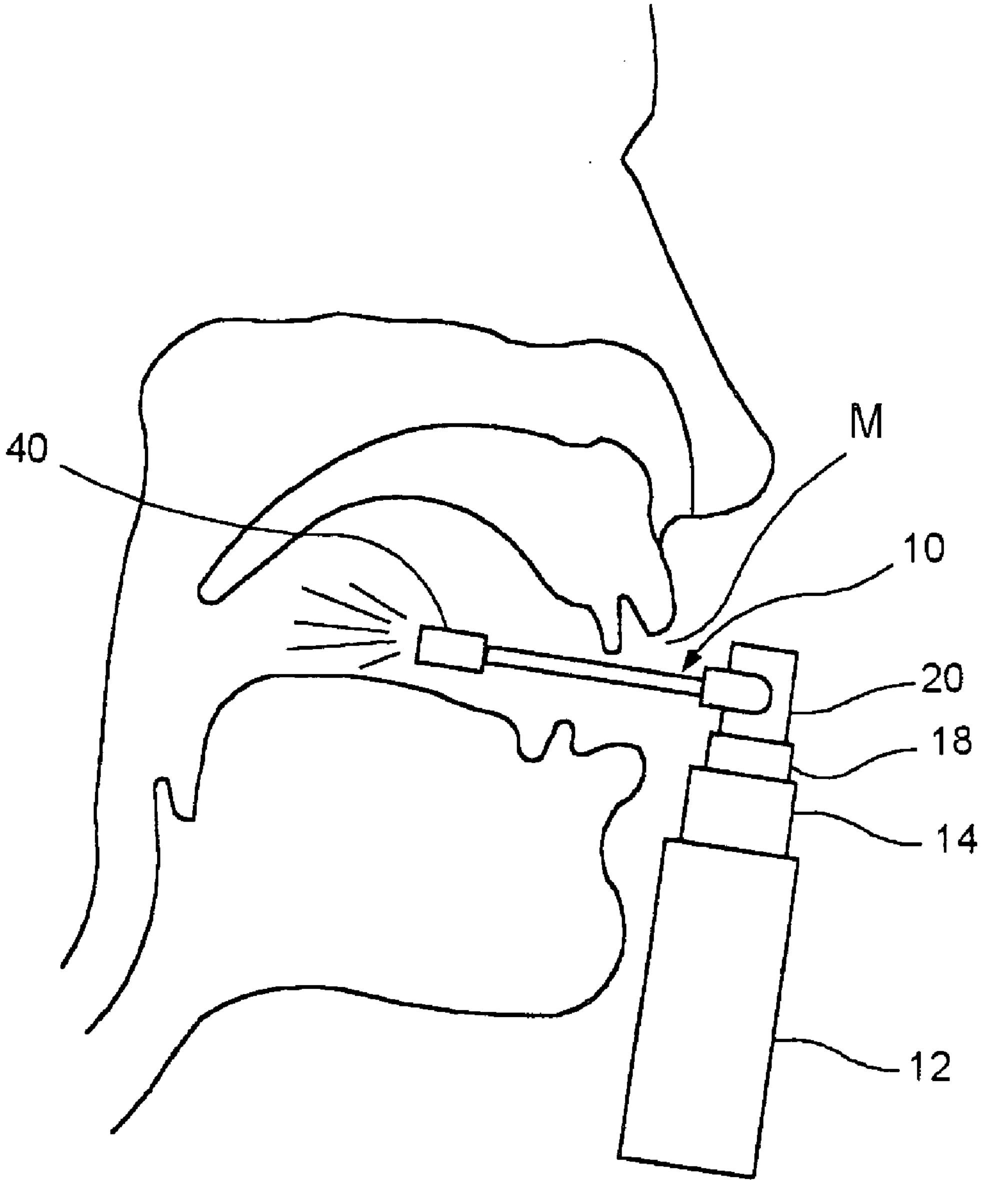
FIG. 5 is a schematic view of a portion human face with the mouth portion shown in phantom and the combined tongue depressor and spray nozzle in the mouth cavity.

Referring now more particularly to FIG. 5 which schematically shows the face of a human in phantom with the mouth orifice open and one embodiment of the combined tongue depressor and spray device positioned inside the mouth M with the combined spray device and tongue depressor above the tongue to prevent the tongue from moving into the way of the spray nozzle.

The tongue depressor positions itself in such a manner to prevent the tongue from moving into engagement with the upper pallet of the mouth so as to prevent the spray or fluid or material as it exits from the dispensing nozzle 40 from reaching the throat and discharging fluid or material or spray towards the throat portion and the rear portion of the tongue. By preventing the material from reaching the throat portion, the intended use of the oral spray which has to reach the throat portion is destroyed.

The tongue depressor central portion 30 has its proximal end attached to the L-shaped rotatable connector 36 for coupling with the pressure member 20.

The tongue depressor as shown in the first embodiment while having a circular configuration has a sufficient diametrical extent to depress the tongue.

Figure 6:
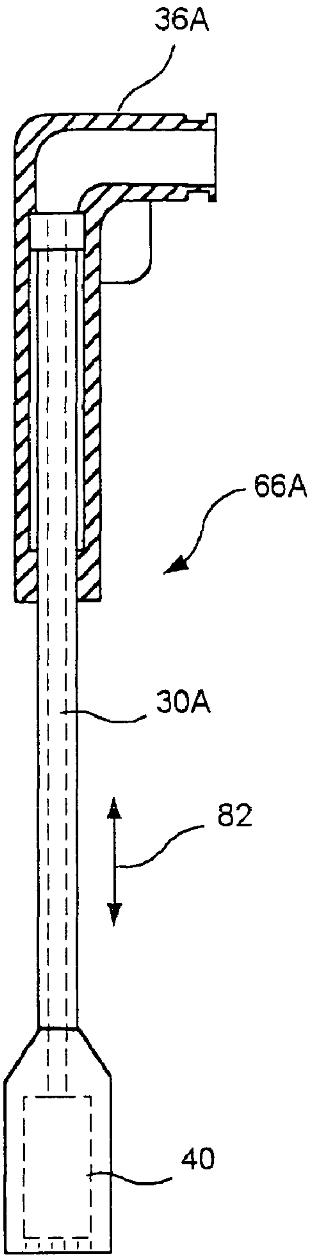
FIG. 6 is a modification of longitudinal tube 30 as shown in FIG. 1 in its collapsed or non-extended condition.
Figure 7:
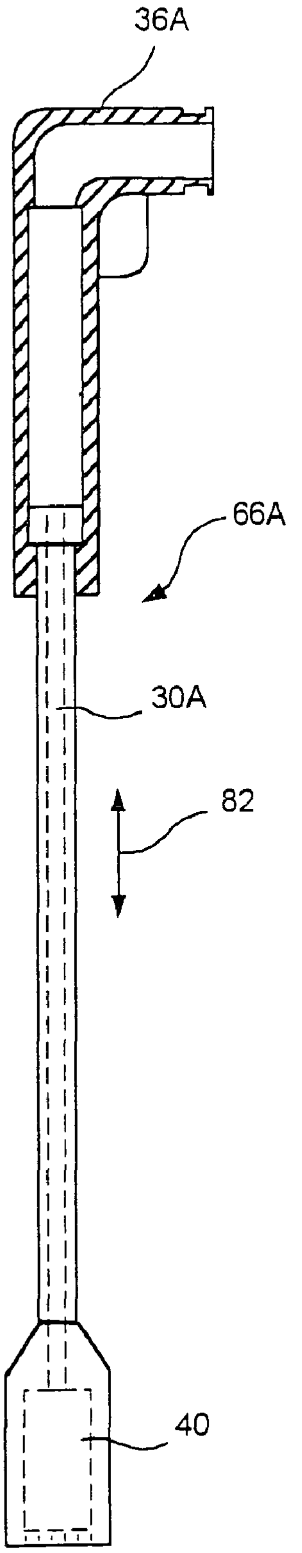
FIG. 7 is another view of the modified longitudinal tube shown in FIG. 6 in its extended condition.

Reference is made to FIGS. 6 and 7 which show a modification of the tongue depressor and oral spray 30 of FIG. 1 and designated 30A, and in which like parts have the same reference numeral throughout and the modified parts have a different or related reference numeral.

In FIGS. 6 and 7, tubular portion 30A is shown as comprising a telescopic arrangement 66 comprising L-shaped member 36A forming an outer telescopic member and the inner tube forms an inner telescopic member 30A. A telescopic arrangement is provided as another embodiment because the mouth portions of an individual can vary, and it is important to reach the rear throat area of the individual user. In particular, when use is intended for a youngster, the length of tubular member 30A is desirably smaller than a connectional size for an adult and the possibility to reduce the longitudinal length is desirable. Double headed arrow 82 shows axial movement of longitudinal tube 30A relative to L-shaped rotatable coupling 36A.

FIG. 6 shows the retracted position and FIG. 7 shows the extended position of the telescopic arrangement.

Referring now to FIGS. 8 to 10 which show a front view, a side view and a bottom view of a modification of dispensing nozzle 40 and is designated 40A and which shows the nozzle 40A with an oval transverse cross-section having a flat bottom or underside portion 80 which is adapted to rest on top of the tongue and provided with openings 42A. Longitudinal tube 30A which also is provided with a flat portion, so as to have it rest on top of the tongue. While in this view reference is made to longitudinal tube 30A, longitudinal tube, 30 in a non-telescopic arrangement can also be used.

Referring now more particularly to FIGS. 11 to 13, which shows a front view of dispenser or spray nozzle 40B having a dispensing opening 42B. In this embodiment, the cross-section of tubular member 40B is substantially circular.

Figure 14:
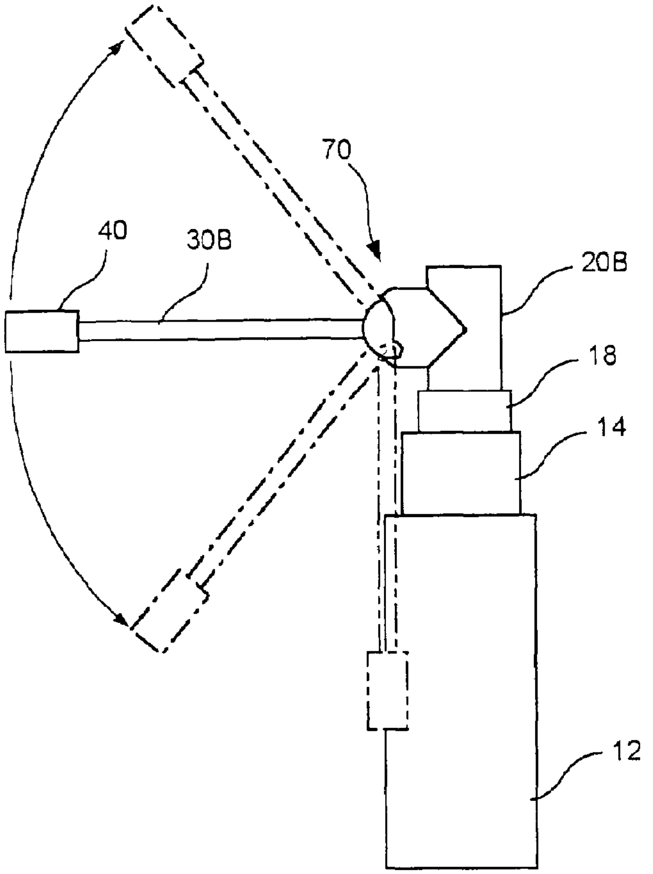
FIG. 14 is a schematic side view of a modification of the combined tongue depressor and oral spray mechanism shown in FIG. 1 and provided with an exit portion connected to the longitudinal tube to provide universal movement in all directions and illustrating the longitudinal tube in three different positions, one of which is in full outline, and the other three in dashed outline to show movement to various different positions.
Figure 16:
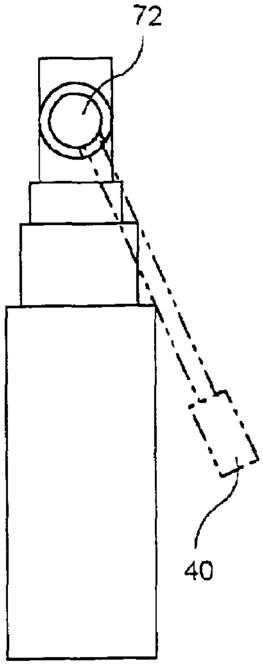
FIG. 16 is a front view of the modification shown in FIG. 14 and illustrating the extension tube displaced from the longitudinal axis of the fluid container.
Figure 15:
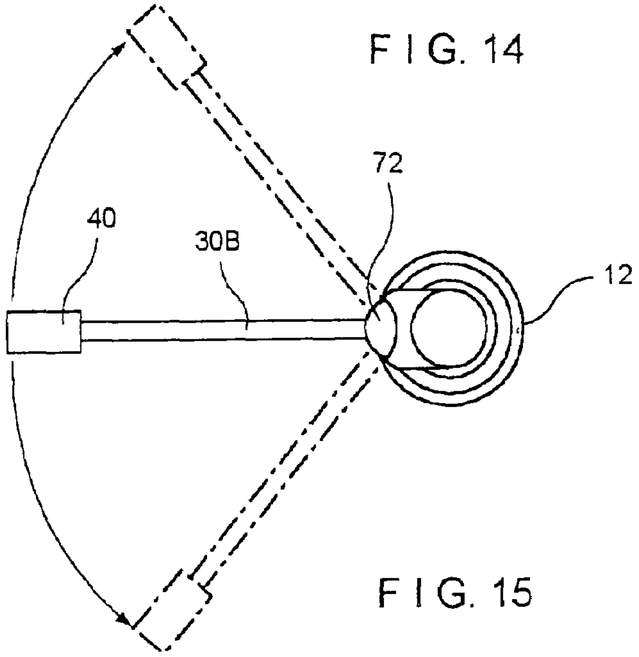
FIG. 15 is a top view of the modification shown in FIG. 14 and illustrating the different positions of the extension tube for movement into different positions showing the extension tube in different positions about a vertical or central axis of the container.

Referring now more particularly to FIGS. 14 to 16 and to FIGS. 17 to 21 which show a detail of FIGS. 14 to 16. Tubular member 30B is coupled with pressure member 20 by means of universal coupler 84 and includes a substantially cylindrical member 86 forming part of universal coupler 84 and connected with tubular member 30C.

Referring now more particularly to FIGS. 17 to 21 which shows the details of the connection of the L-shaped fluid guide member 34. In this embodiment, L-shaped member 34 is angularly arranged with respect to pressure member 20 so that all different possible angular movement of L-shaped member 34 relative to pressure member 20 is made possible.

Figure 17:
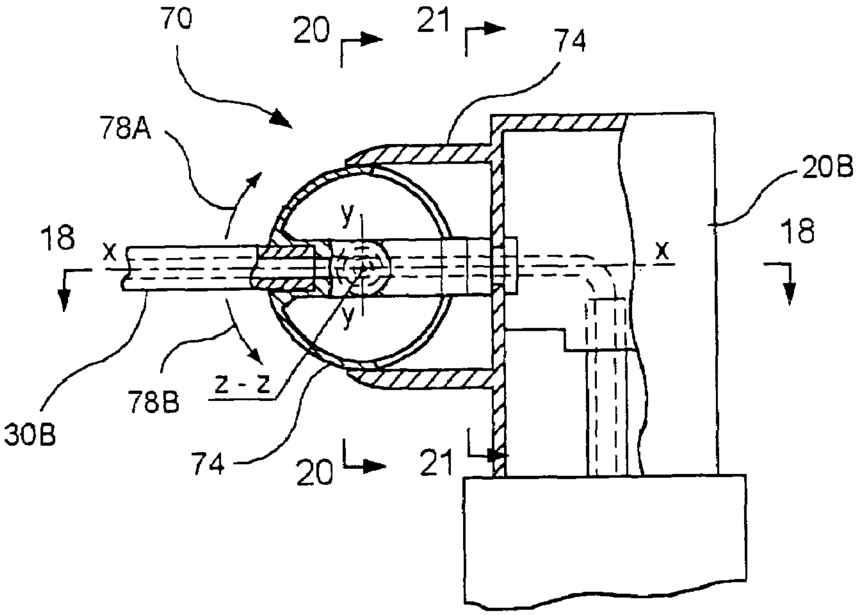
FIG. 17 is a partial elevational view shown partially in section to illustrate in detail the structure for the material dispensing arrangement between the container and the tongue depressor portion so that the dispenser can be moved in all directions.

Pressure member 2 is provided with a substantially cylindrical housing 74 for receiving a cylindrical member 20. In FIG. 17, L-shaped guide member 34 is shown in a center position and is movable in either direction as shown as arrows 78A, 78B, and in FIG. 19, arrow 79C shows the movement in both directions. Tube 30B is rotatable in all directions.

The tongue depressor as shown can have a rectangular cross-sectional configuration or a square cross-sectional configuration having a flat portion similar to flat portion 80 which is adapted to rest on top of the tongue if necessary.

The device is made from a readily available synthetic material which has no deleterious effect on the mouth cavity.

The combined tongue depressor spray nozzle is utilized together with the container by a user who holds the container in their hand and places the tongue depressor spray nozzle into the mouth cavity with the nozzle towards the rear of the mouth and back of the tongue. It is well known that bacteria embeds itself on the tongue and that the rear or dorsal portion of the tongue is difficult to reach.

Closure member 14 is provided with an outer surface having a gripping surface so that the closure 14 can be easily opened and removed from container 12.

The entire tongue depressor and oral spray device is quite compact for ease of carrying with the container, as well as ease of use. The central portion 12 is typically and preferably about 3 inches long so that the rear portion of the throat and the dorsal portion of the tongue can be reached.

The universal coupler 84 comprises a canter levered pulley 86 in the form of a circular lug connected to the vertical wall 20A of the pressure member 20 in a manner that pulley 86 can only be rotated about axis X-X, designated 86. Cylindrical member 88 is a hollow ball provided with a projection 90 directed to and approximately at the center of the ball or cylindrical member 88.

Projection 90 is provided with two material flow paths 90A and 90B which merge into a single flow path 90C at the right end. At the right end, as viewed in the drawing, both paths which merge communicate with L-shaped fluid or material guide member 34.

Figure 18:
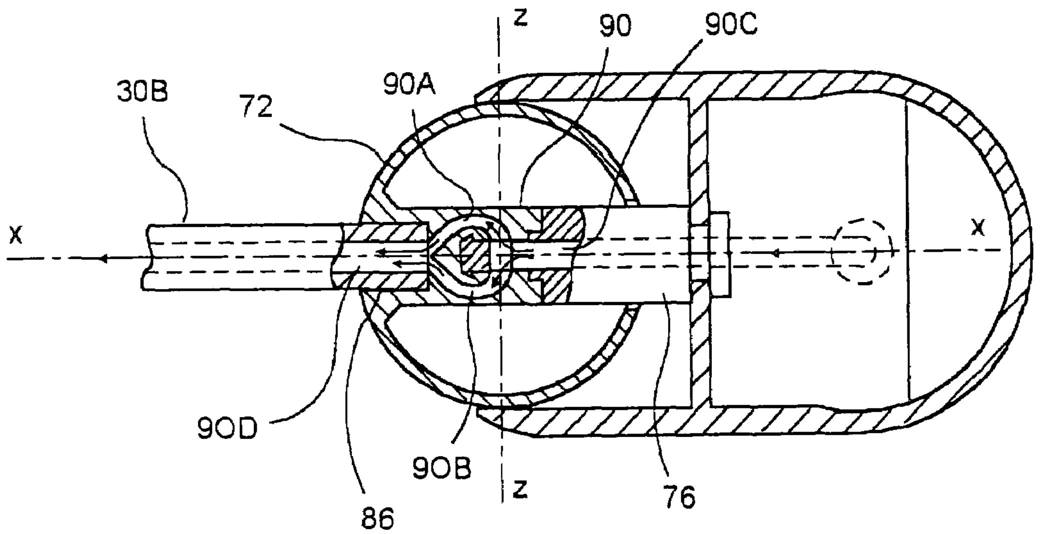
FIG. 18 is a sectional view taken along line 18-18 of FIG. 17.

At the left end, both paths 90A and 90B merge into a single flow path 90D as viewed in the drawing in FIG. 18. At the left end, path 90D is connected with central opening 32 in tube 30B.

As shown, circular lug 76 is rotatable about axis X-X in wall 20A and both tube 30B and cylindrical member 72 are rotatable together about axis X-X (FIG. 18). Tube 30B and cylindrical member 72 together they provide a hinge joint and allow rotation of canterlevered pulley 76 about axis Z-Z, see FIGS. 17 and 18. In this manner, the cylindrical member 76 and tubular member 30B can rotate or swivel or move in all directions to facilitate ease of holding container 12 and application of the combined tongue depressor and spray device.

It will be readily appreciated that the tongue depressor and oral spray provides a unique mechanism in order to reach all portions of the tongue as well as the throat cavity. For this purpose, it is preferred that device 10 have a length of approximately one inch to three inches so that the rear portion of the tongue, throat portion and tonsil area can be reached. The smaller extent is desired for a child where the length from the front of the mouth to the throat area is of a lesser extent.

It is to be understood that the detailed descriptions of the various embodiment of the inventions are provided merely by way of example, and it will be further appreciated that various changes and modifications may be made without departing from the scope of the invention.

The invention claimed is:

1. A combined tongue depressor and oral spray device adapted to be connectable to a container containing an oral spray material to enable fluid contents contained within the container to be dispensed through the tongue depressor and oral spray device to reach the throat cavity and the rear portion of the tongue, comprising:

a longitudinal tube member including a tongue depressor portion comprising an outer surface with a substantially flat surface for contact with a tongue for depression thereof and having an inner passageway extending from a proximal end thereof to a distal end thereof;

means for connecting the proximal end to the container for permitting movement of the longitudinal tube relative to the container; and exit means associated with the distal end of said longitudinal tube for permitting material contained in the container to exit from the container and through said tube and out of said exit means to reach the rear of the tongue and the throat cavity and the rear of the mouth.

2. The device as claimed in claim 1, wherein said inner passageway is a central opening passing from the proximal end to the distal end.

3. The device as claimed in claim 1, wherein the exit means of said tongue depressor includes a nozzle portion having one end for connection with said longitudinal tube member and another end including an aperture fluid dispensing portion.

4. The device as claimed in claim 3, wherein the aperture fluid dispensing portion at the end of said tongue depressor includes a plurality of openings inwardly displaced from an outer rim portion of said other end and communicating with said container through said passageway in said longitudinal tube member.

5. The device as claimed in claim 1 wherein said means for connecting said proximal end to said container includes a closure cap for said container and a movable connector mechanism having one portion of a universal connecter mechanism connected to said proximal end and another portion movably connected to said closure cap to provide relative movement of said longitudinal member relative to said closure cap.

6. The device as claimed in claim 5 wherein said movable connector is an L-shaped member having an inner passageway extending from one end to the other, and one end of said inner passageway being in fluid or material communication with the inner passageway of said longitudinal member and the other end of L-shaped member being in fluid or material communication with the opening of said second member.

7. The device as claimed in claim 6, wherein said second member and said second means include cooperating elements to permit said longitudinal member to be rotated about a longitudinal axis passing through the opening associated with said second member.

8. The device as claimed in claim 1 wherein the length of said longitudinal tube is at least as long as a conventional adult tongue to enable the exit means to reach the throat portion and enable the user to hold the container free of pressure against the user's body portion.

9. The device as claimed in claim 1, wherein the length of the longitudinal tube member is adjustable and includes a pair of coaxial members telescopically arranged for adjustment of the longitudinal length.

10. A combined tongue depressor and oral spray mechanism adapted to be connectable to a container containing an oral spray fluid to enable fluid contents contained within the container to be dispensed as a jet spray through the tongue depressor oral spray mechanism to reach the throat cavity and the rear portion of the tongue, comprising:

a combined tongue depressor and oral spray mechanism including a longitudinal tube member having an inner passageway extending from a proximal and thereof to a distal end thereof and an outer surface configuration with a substantially flat surface for engagement with the top surface of the tongue to prevent any part or portion of the tongue from interfering with the spray discharged from the discharge nozzle at the distal end;

means for connecting the proximal end to the container for permitting movement of the longitudinal tube relative to the container for movement through an arc of 360°;

exit means associated with the distal and of said longitudinal tube for permitting the fluid contained in the container to exit from the container and through the distal end of said tube and out of said exit means to reach the rear of the tongue and the throat cavity and the rear of the mouth proximate to the tonsils; and wherein the length of said longitudinal tube member is longitudinally adjustable along a central axis, at least as long as a conventional adult tongue and approximately one to three inches to enable the exit means to reach the throat portion and enable the user to hold the container free of pressure against the user's body portion.

11. The device as claimed in claim 10, wherein said inner passageway is a central opening passing from the proximal end to the distal end for providing a fluid connection with said container and the exit means.

12. The device as claimed in claim 10, wherein the exit means includes a nozzle portion having one end for connection with said longitudinal tube member and another end including an aperture liquid dispensing portion having a plurality of openings peripherally arranged and spaced about a central axis of said longitudinal tube member providing direct communications with said inner passageway.

13. The device as claimed in claim 12, wherein said plurality of openings are provided on a dispenser-nozzle and are inwardly displaced from an outer rim portion of said dispenser nozzle on said other end and communicating with said container through said passageway in said longitudinal tube member, said dispenser nozzle having an outer circumference substantially coextension with the outer surface of said longitudinal tube member.

14. The device as claimed in claim 10 wherein said means for connecting said proximal end to said container includes a closure cap for said container and a connector mechanism having one portion connected to said proximal end and another portion connected to said closure cap, said connection means having an inner aperture in communication with the inner passageway of said longitudinal member.

15. A combined tongue depressor and oral spray device adapted to be connectable to a container containing an oral spray material to enable fluid contents contained within the container to be dispensed through the tongue depressor oral spray device to reach the throat cavity and the rear portion of the tongue, comprising:

a longitudinal tube member having an inner passageway extending from a proximal end thereof to a distal end thereof;

means for connecting the proximal end to the container for permitting movement of the longitudinal tube member relative to the container;

exit means associated with the distal end of said longitudinal tube member for permitting material contained in the container to exit from the container and through said longitudinal tube member and out of said exit means to reach the rear of the tongue and the throat cavity and the rear of the mouth; and said longitudinal tube member having a shape with at least one flat side adapted for resting on the tongue to prevent the tongue from blocking the exit spray material and enabling said exit spray material to reach the rear of the mouth cavity and the rear portion of the tongue.

16. A combined tongue depressor and oral spray device adapted to be connectable to a container containing an oral spray material to enable fluid contents contained within the container to be dispensed through the tongue depressor oral spray device to reach the throat cavity and the rear portion of the tongue, comprising:

a longitudinal tube member having an inner passageway extending from a proximal end thereof to a distal end thereof;

means for connecting the proximal end to the container for permitting movement of the longitudinal tube member relative to the container;

exit means associated with the distal end of said longitudinal tube member for permitting material contained in the container to exit from the container and through said tube member and out of said exit means to reach the rear of the tongue and the throat cavity and the rear of the mouth;

said means for connecting said proximal end to said container includes a closure cap for said container and a movable connector mechanism having one portion of a universal connecter mechanism connected to said proximal end and another portion movably connected to said closure cap to provide relative movement of said longitudinal tube member relative to said closure cap; and said closure cap includes a first member substantially relatively non-movable such that said closure cap is closed on said container and a second member telescopically associated with said first member for movement relative to said first member to decrease the volume of the container and said second member to cause the material to be expelled from said container through an opening associated with said second member, and said movable connector includes first means for connection of said movable connector with said longitudinal tube member and second means for connection with the opening in said second member and having an opening in communication with the opening associated with said second member for causing the material to be transmitted to said inner passageway in said longitudinal tube member.

17. A combined tongue depressor and oral spray mechanism adapted to be connectable to a container containing an oral spray fluid to enable fluid contents contained within the container to be dispensed as a jet spray through the tongue depressor oral spray mechanism to reach the throat cavity and the rear portion of the tongue, comprising:

a longitudinal tube member having an inner passageway extending from a proximal and thereof to a distal end thereof;

means for connecting the proximal end to the container for permitting movement of the longitudinal tube member relative to the container for movement through an arc of 360°;

exit means associated with the distal and of said longitudinal tube for permitting the fluid contained in the container to exit from the container and through the distal end of said tube and out of said exit means to reach the rear of the tongue and the throat cavity and the rear of the mouth proximate to the tonsils; and said longitudinal tube member having a quadrilateral shape in cross-section transverse to its longitudinal axis with at least one flat side adapted for resting on the tongue to prevent the tongue from blocking the exit spray from reaching the rear of the mouth cavity and the rear portion of the tongue.

18. A combined tongue depressor and oral spray mechanism adapted to be connectable to a container containing an oral spray fluid to enable fluid contents contained within the container to be dispensed as a jet spray through the tongue depressor oral spray mechanism to reach the throat cavity and the rear portion of the tongue, comprising:

a longitudinal tube member having an inner passageway extending from a proximal and thereof to a distal end thereof;

means for connecting the proximal end to the container for permitting movement of the longitudinal tube member relative to the container for movement through an arc of 360°;

exit means associated with the distal and of said longitudinal tube member for permitting the fluid contained in the container to exit from the container and through the distal end of said tube and out of said exit means to reach the rear of the tongue and the throat cavity and the rear of the mouth proximate to the tonsils; and said longitudinal tube member having a quadrilateral shape in cross-section transverse to its longitudinal axis with at least one flat side adapted for resting on the tongue to prevent the tongue from blocking the exit spray from reaching the rear of the mouth cavity and the rear portion of the tongue.

19. The device as claimed in claim 18, wherein said means connecting said proximal end to said container includes a universal connector having a pair of fluid passageways coupling a fluid passageway in the closure cap with a fluid passageway in the longitudinal tube member and wherein the longitudinal tube member is axially adjustable.

20. A combined tongue depressor and oral spray device adapted to be connectable to a container containing an oral spray material to enable fluid contents contained within the container to be dispensed through the tongue depressor oral spray device to reach the throat cavity and the rear portion of the tongue, comprising:

a longitudinal tube member having an inner passageway extending from a proximal end thereof to a distal end thereof;

means for connecting the proximal end to the container for permitting movement of the longitudinal tube member relative to the container;

exit means associated with the distal end of said longitudinal tube for permitting material contained in the container to exit from the container and through said tube and out of said exit means to reach the rear of the tongue and the throat cavity and the rear of the mouth; and said means connecting said proximal end to said container includes a universal connector having a pair of fluid passageways coupling a fluid passageway in the closure cap with a fluid passageway in the longitudinal tube member and wherein the longitudinal tube member is axially adjustable.

* * * * *